United States Patent [19]
Novikov et al.

[11] 3,966,742
[45] June 29, 1976

[54] TETRA-N-ALKYL DERIVATIVES OF BICYCLIC UREAS AND METHOD OF THEIR PRODUCTION

[76] Inventors: Sergei Sergeevich Novikov, Kotelnicheskaya naberezhnaya, 1/5, kv. 183; Lenor Ivanovich Khmelnitsky, ul. Miklukho-Maklaya, 57, korpus 1, kv. 139; Oleg Vasilievich Lebedev, ul. Obrucheva, 9, kv. 83; Lia Vladimirovna Epishina, Bolotnikovskaya 40, korpus 1, kv. 16; Ljudmila Ivanovna Suvorova, B. Ostroumovskaya, 15, kv. 24, all of Moscow; Lidia Vasilievna Lapshina, Podolsky raion, p/o Ryazanovo, dom otdykha ostafievo, 17, Moskovskaya oblast; Valery Dmitrievich Krylov, ul. Uralskaya, 17, kv. 150, Moscow; Irina Vitalievna Zaikonnikova, ul. Chekhova, 4b, kv. 1, Kazan; Irina Evgenievna Zimakova, ul. Lenina, 2a, kv. 18, Kazan; Vladimir Sergeevich Chudnovsky, ul. Dekabristov, 189, kv. 5, Kazan; Viktor Andreevich Babichev, Komsmolsky prospekt, 38/16, kv. 81, Moscow; Nina Alexandrovna Avdonina, ul. Gagarina, 14, kv. 3, Kazan, all of U.S.S.R.

[22] Filed: July 27, 1972

[21] Appl. No.: 275,823

[52] U.S. Cl. .................. 260/256.4 F; 260/309.7; 424/251; 424/273
[51] Int. Cl.$^2$.................................. C07D 239/04
[58] Field of Search .................. 260/309.7, 256.4 F

[56] References Cited
FOREIGN PATENTS OR APPLICATIONS
635,435   1/1964   Belgium
36-21743   11/1961   Japan OTHER PUBLICATIONS
J. Org. Chem. 28: 2378–2380 (1963), Nematollahi et al.
C.A. 59:12786c (1963) Nematollahi et al.
Bull Soc. Chem. Fr. (1971) 211–214, Renault et al.
C.A. 74:99835p (1971) Renault et al.

*Primary Examiner*—Sherman D. Winters
*Attorney, Agent, or Firm*—Haseltine, Lake & Waters

[57] ABSTRACT

A method for producing tetra-N-alkyl derivatives of bicyclic ureas having the general formula:

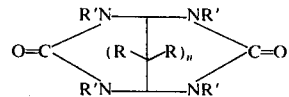

wherein $n$ is 0 or 1; R and R' is H, lower alkyls, which can be the same or different, characterized in that bicyclic ureas, unsubstituted at nitrogen atoms are alkylated with alkyl halides in liquid ammonia under the action of an alkali metal amide, followed by separation of the target product.

Said tetra-N-alkyl derivatives of bicyclic ureas are pharmacologically active compounds. The most active representative of said compounds, 2,4,6,8-tetramethyl-2,4,6,8-tetraazabicyclo-3,3,0-octanedi-3,7-one, is the active principle of a medicinal preparation used for treating psychic disorders.

8 Claims, No Drawings

TETRA-N-ALKYL DERIVATIVES OF BICYCLIC UREAS AND METHOD OF THEIR PRODUCTION

The present invention is related to a method for producing tetra-N-alkyl derivatives of bicyclic ureas, novel tetra-N-alkyl derivatives of bicyclic ureas, and application of 2,4,6,8-tetramethyl-2,4,6,8-tetraazabicyclo-/3,3,0/-octanedi-3,7-one.

Tetra-N-alkyl derivatives of bicyclic ureas having the general formula:

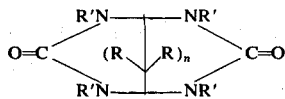

wherein $n$ is an integer 0 or 1; R and R' = H; lower alkyls that can be the same or different, are pharmacologically active compounds, possessing distinct neuroleptic activity and find application in medicine.

Known in the art are methods for producing tetra-N-alkyl derivatives of bicyclic urea — 2,4,6,8-tetramethyl-2,4,6,8-tetraazabicyclo-/3,3,0/-octanedi-3,7-one. One of the above methods comprising alkylating with dimethylsulphate 2,4,6,8-tetraazabicyclo-/3,3,0/-octanedi-3,7-one in a boiling alkaline medium, followed by extraction of the product thus obtained with benzene and its recrystallization from dioxane. The yield of the target product is 20 weight percent, as calculated for unpurified product.

Another method of producing 2,4,6,8-tetramethyl-2,4,6,8-tetrazabicyclo-/3,3,0/-octanedi-3,7-one consists in that N,N'-dimethylurea is condensed with glyoxal in an aqueous medium in the presence of hydrochloric acid, followed by separation of the target product. The yield of crude target product is about 1 weight percent.

A disadvantage of the above methods lies in low yield of the target product, unsuitability of the technology described for the production of other tetra-N-alkyl derivatives of bicyclic ureas, as well as impossibility of implementing these methods on an industrial scale.

It is an object of the present invention to increase the yield of the target products and to provide a method suitable for industrial application. Said object is accomplished by that in a method for producing tetra-N-alkyl derivatives of bicyclic ureas having the general formula:

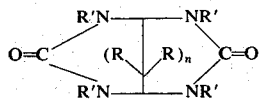

wherein $n$ is an integer 0 or 1; R and R' is H; lower alkyls can be the same or different, wherein according to the present invention bicyclic ureas, unsubstituted at the nitrogen atoms, are alkylated with alkyl halides in liquid ammonia under the action of an alkali metal amide.

The alkyl halide preferably used according to the invention is alkyl iodide.

The alkali metal amide most advantageously used is sodium amide.

The alkali amide may be used in the form of a ready for use reagent or else it may be prepared in situ in the course of the reaction by adding an alkali metal to liquid ammonia in the presence of ferric chloride hexahydrate.

The process is preferably carried out in the presence of alkali metal halides, such as sodium chloride or sodium iodide. The process is carried out as follows.

To a suspension comprising bicyclic urea, unsubstituted at nitrogen atoms, and an alkali metal amide in liquid ammonia cooled to minus 50° to 60°C is added, while stirring, an alkyl halide which is preferably alkyl iodide. The mixture is allowed to stand for from 40 minutes to one hour. To accelerate the reaction, it is expedient to add alkali metal halides, for example, sodium chloride or sodium iodide. The reaction mixture is subjected to boiling until all liquid ammonia is evaporated. Then water is added to the residue and the latter is repeatedly extracted with an organic solvent.

The solvent is then distilled off, and the target product is isolated. The process yields up to 86 weight percent of crude target product; the yield of purified product reaching 75 weight percent. The process disclosed increases the yield of the target product, and can be used on a commercial scale.

Novel tetra-N-alkyl derivatives of bicyclic ureas, corresponding to the general formula

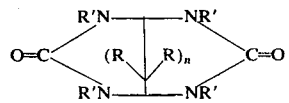

wherein with $n$ being 0, R' is a lower alkyl $C_2 - C_4$; and with $n$ being 1, R and R' are H; lower alkyl, can also be produced by said method.

These novel compounds are colourless crystalline substances, readily soluble in water, alcohol and methylene chloride.

The above compounds exhibit pronounced neuroleptic properties. The most active tetra-N-alkyl derivative of bicyclic ureas is 2,4,6,8-tetramethyl-2,4,6,8-tetraazabicyclo-/3,3,0/-octane) -3,7-one, is the active principle of a medicinal preparation for treating mental disorders.

This preparation is used for treating persistent cases of verbal hallucinations in the presence of moderately affective fluctuations in the absence of a marked psycho-motoric excitement, as well as for psychoses with predominating affective disorders, including hypomaniacal conditions in maniacal-depressive psychosis and in the circular form of schizophrenia; anxiety in involutional depression, and psychoses stemming from cerebrovascular pathology, and in organic cerebral affections; endogenic depression with delusions and paranioc symptoms.

By its psycho-sedative effect the compound is weaker than the widely known so-called high or strong tranquilizers, (Aminazine, Tisercine, Haloperidol, Tropacine, etc.), however it is stronger than the so-called low or weak tranquilizers (Elenium, Seducsene, Meprobamate, etc.).

The present compound exhibits low toxicity. The lethal dose for 100 white mice is 5500 mg/kg; that for 50 white mice—3800 mg/kg. The maximum tolerable dose (MTD) is 3000 mg/kg.

In experiment, the preparation suppressed the investigatory reaction intensity of white mice by about 8 times as compared with the normal response upon the introduction ½ MTD 2 hours prior to the beginning of the test, increasing the length of the chloral hydrate-induced sleep 9times when administered 1/5 MTD.

The medicinal preparation was clinically tested on 14 patients. It was prescribed as a tranquillizer for psychic disorders, the illness being mainly manifested by psycho-motoric excitation, affective disorders, delusions and verbal hallucinations syndrome. To the treatment were subjected patients with the following forms of mental disorders: schizophrenia — 3 cases; involutional depression — 2 cases; maniacal-depressive psychosis — 4 cases; organic cerebral affection with verbal hallucinations syndrome — 3 cases, epileptic insanity — 1 case; atherosclerotic psychosis with anxiety depression syndrome — 1 case.

The preparation was prescribed per os in doses of 0.3 to 1.0 g three times a day, or alternatively intramuscularly in the form of a 10% solution, in doses of 3 to 6 ml. two or three times a day. The duration of treatment was from 10days to 1.5 months. Two patients suffering from an acute psychomotoric excitement were administered the preparation intravenously in the form of a 10% solution, in doses of 3 to 6 ml. two-three times a day, for a period of several days, followed by the intramuscular injection of the preparation. In the course of treatment with the preparation, systematic analyses were taken of the patients urea and blood; the pulse, blood pressure and body temperature were taken three times a day.

From the very first days the condition of the patients improved. Patients with the hypomaniacal syndromes showed better mood, reduced motoric activity, their behaviour became more organized and orderly. In treating the patients with the anxiety depression syndrome the effect of the preparation manifested itself in the abatement and disappearance of anxiety, agitation, and unfounded fear. Where verbal hallucination symptoms were predominant, first there was observed a tranquillizing effect (the patient became less anxious and restless), then the hallucinations weakened until they completely disappeared.

In patients with intensive catatonic, maniacal and epileptic excitation, no therapeutic effect could be noted. Somatic examination of patients in the course of treatment with the preparation revealed a 1° to 1.5°C drop of temperature during the first few days. Some patients showed an insignificant and temporary drop of blood pressure. No changes were revealed in the urea and blood pictures.

According to the invention, the medicinal preparation contains the active principle and a pharmaceutic solvent or, in case of tablets, a filler.

The solvent preferably used is water. The content of the active principle in solution is 10 percent.

The pharmaceutical filler for tablets is starch or sugar powder. The tablets preferably contain from 0.25 to 0.5 g of the active principle. The preparation can be used in the form of a powder, tablets or in the form of intramuscular and intravenous injections. It is prescribed to be taken two or three times a day, per 1.0 to 1.5 g. Parenteral injections of the preparation are painless and do not provoke any local inflammatory reaction.

Aqueous solutions of the preparation are stable against sterilization. The preparation does not exhibit any cumulative properties, does not cause any morphological changes of the viscera, and is removed from the organism within 24 hours. The preparation does not cause any side effects.

A better understanding of the present invention will be had from the following examples of carrying out the method for the producton of tetra-N-alkyl derivatives of bicyclic ureas.

EXAMPLE 1

To a suspension of 42.6 g. (0.3 moles) of 2,4,6,8-tetraazabicyclo-/3,3,0/-octanedi-3,7-one (glycoluryl), 17.5 g. (0.3 moles) of sodium chloride, 46.8 g. (1.2 moles) of sodium amide in 1,000 ml. of liquid ammonia, stirred and cooled to minus 50° to 60°C, a solution of 268.6 g. (112.8 ml. — 1.87 mols) of freshly distilled methyl iodide in 120 ml. of dry ether was added over a one-hour period, thereupon the mixture was allowed to stand at the same temperature for 40 minutes; to the mixture was then added 20 g. of ammonium chloride and the resulting mixture was boiled until the liquid ammonia completely evaporated. To the residue was added 25 ml of water and it was repeatedly extracted with methylene chloride (10 times with 200 ml.); the solvent is then evaporated thus giving 50 g. (80 weight percent) of 2,4,6,8-tetramethyl-2,4,6,8-tetraazabicyclo-/3,3,0/-octanedi-3,7-one. The yield of pure product is 30 g. (50 weight percent), melting point — 228°C (from abs. ethanol). The melting point given in literature is 225° to 227°C. A mixed sample of the novel product with 2,4,6,8-tetraazabicyclo-/3,3,0/-octanedi-3,7-one obtained by the known method does not show a depression of the melting point.

EXAMPLE 2

To a suspension of 42.6 g. (0.3 mols) of 2,4,6,8-tetraazabicyclo-/3,3,0/-octanedi-3,7-one in 1,000 ml. of liquid ammonia cooled to minus 50° to 60°C was added in small portions 23.5 g. (0.6 mol) of sodium amide and then 85 g. (38.0 ml. −0.6 mol) of methyl iodide in 60 ml. of ethyl ether was added dropwise. 10 minutes after the addition of methyl iodide, another 23.5 g. (0.6 mol) of sodium amide was added, followed by the addition of the solution of 183.6 g. (74.8 ml. — 1.27 mols) of methyl iodide in 60 ml. ot ether. Similar to the first step, the formed mixture was allowed to stand for 40 minutes. Further the process of separation is carried out as described in example 1.

The yield of crude 2,4,6,8-tetramethyl-2,4,6,8-tetrazabicyclo-/3,3,0/-octanedi-3,7-one is 50 g. (80 wt.%), and that of purified target product is 30 g. (50 wt.%), m.p. 228°C (from alcohol).

EXAMPLE 3

To a suspension of 14.2 g. (0.1 mol) of glycoluryl and 15.0 g (0.1 mol) of sodium iodide in 700 ml. of liquid ammonia were added, while stirring the reaction medium and cooling it to a temperature of −30° to −40°C, 9.2 g. (0.4 mol) of sodium metal in the form of 0.5 g. pieces, 0.2 g. of potassium metal, and 0.006 g. of ferric chloride hexahydrate. After complete discoloration of the initially dark-blue reaction mixture, this discoloration being indicative of the formation of sodium and potassium amide, to the reaction mixture cooled to a temperature of −50° to −60°C was added, over a period of one hour, a solution of 93.6 g. (0.6 mol) of freshly distilled ethyl iodide in 60 ml. of anhydrous ether, followed by maintaining the mixture at this temperature for 40 minutes, adding thereto 6 g. of ammonium chloride, and thereafter evaporating the mixture to remove all the liquid ammonia. Next the residue was taken up in 10 ml. of water and repeatedly extracted with methylene chloride (10 portions of 50 ml. each). The solvent was evaporated to yield 6.7 g (24 wt.%) of 2,4,6,8-tetraethyl-2,4,6,8-tetraazabicyclo-/3,3,0/-octandi-3,7-one. The yield of the pure product was 3.4 g (12 wt.%); m.p. 107°–108°C (from cyclohexane).

EXAMPLE 4

From 15.6 g. (0.01 mols) of 2,4,6,8-tetraazabicyclo-/3,3,1/-nonanedi-3,7-one, m.p. 305° to 306°C. (with decomp.) there were produced 16.9 g (yield — 80 weight percent) of 2,4,6,8-tetramethyl-2,4,6,8-tetraazabicyclo-/3,3,1/-nonanedi-3,7-one; by following the procedure similar to that of Example 1. The yield of pure product was 13.6 g. (64 weight percent), m.p. 319° to 320°C. (with decomp. from amyl alcohol). Rf = 0.72 (carrier — silicagel; solvent — alcohol: 25% ammonia solution = 7:1, development with iodine vapours). The product is easily soluble in chloroform, methylene chloride, water; insoluble in benzene, ether, hexane.

Found, %: C, 50.85; H, 7.62; N, 26.59. $C_9H_{16}N_4O_2$. Calculated, %: C, 50.93; H, 7.60; N, 26.40.

IR spectrum: 2975, 2950, 2900, 2850, 1650, 1630, 1620, 1560; 1505; 1490, 1440, 1415, 1410, 1390, 1345, 1275, 1250, 1230, 1195, 1125, 1070, 1050, 980, 905, 765, 735, 680, 650, 618, 565, 510, 455, 415 $cm^{-1}$.

PMR spectrum taken in chloroform (hexamethyldisiloxale as reference) corresponds to the structure and contains a singlet ($\delta = 3.2$ ppm), two triplets ($\delta = 4.58$ ppm and $\delta = 2.30$ ppm; I = 3 Hz), the intensity ratio being 6:1:1.

EXAMPLE 5

From 18.4 g. (0.1 mol) of 9,9-dimethyl-2,4,6,8-tetraazabicyclo-/3,3,1/-nonanedi-3,7-one, m.p. = 360°C there were produced 20 g. (yield — 86 weight percent) of 2,4,6,8,9,9-hexamethyl-2,4,6,8-tetraazabicyclo-/3,3,1/-nonanedi-3,7-one, by following the procedure outlined in Example 1. The yield of pure product was 17.6 g. (73 weight percent). M.p. 285° to 287°C (from an acetone-/ethanol mixture). Rf = 0.67 (carrier —silicagel, solvent — alcohol, development with iodine vapors).

Found, %: C, 55.12; H, 8.55; N, 23.30. $C_{11}H_{20}N_4O_2$. Calculated, %: C, 54.98; H, 8.39; N, 28.32.

IR spectrum: 2970, 2925, 2900, 2875, 1680, 1670, 1660, 1650, 1630, 1620, 1540, 1520, 1505, 1490, 1480, 1418, 1395, 1370, 1280, 1225, 1190, 1160, 1120, 1030, 960, 940, 910, 820, 800, 755, 565, 535, 490, 450, 420 $cm^{-1}$.

PMR spectrum of the substance taken in deuterochloroform (hexamethyldisiloxane as reference) corresponds to the structure and contains three singlets ($\delta = 1.18; 3.07; 3.94$ ppm); the intensity ratio being 3:6:1.

What we claim is:

1. A method for producing tetra-N-alkyl derivatives of bicyclic ureas having the formula:

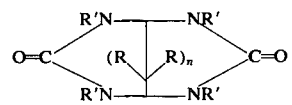

wherein $n$ is an integer 0 or 1, R is selected from the group consisting of H and lower alkyl which can be the same or different, and R' is lower alkyl comprising alkylating bicyclic ureas, unsubstituted at the nitrogen atoms, with lower alkyl halides in liquid ammonia under the action of an alkali metal amide, followed by separation of the product.

2. A method as claimed in claim 1, wherein said alkyl halide is alkyl iodide.

3. A method as claimed in claim 1, wherein said alkali metal amide is sodium amide.

4. A method as claimed in claim 1, wherein said process is carried out in the presence of alkali metal halides.

5. A method as claimed in claim 4, wherein said alkali metal halide is sodium chloride.

6. A method as claimed in claim 4, wherein said alkali metal halide is sodium iodide.

7. A tetra-N-alkyl derivative of a bicyclic urea having the formula:

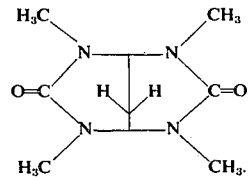

8. A tetra-N-alkyl derivative of a bicyclic urea having the formula:

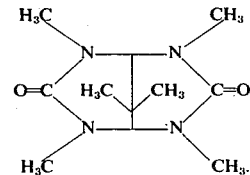

* * * * *